(12) United States Patent
Ensign

(10) Patent No.: US 8,192,393 B2
(45) Date of Patent: Jun. 5, 2012

(54) METHOD AND APPARATUS FOR INSERTING A RECTAL SUPPOSITORY

(75) Inventor: Jennifer Davagian Ensign, Sudbury, MA (US)

(73) Assignee: Christcot Medical Company, Sudbury, MA (US)

( * ) Notice: Subject to any disclaimer, the term of this patent is extended or adjusted under 35 U.S.C. 154(b) by 430 days.

(21) Appl. No.: 12/287,215

(22) Filed: Oct. 7, 2008

(65) Prior Publication Data

US 2010/0087797 A1    Apr. 8, 2010

(51) Int. Cl.
*A61M 31/00* (2006.01)

(52) U.S. Cl. .......................... 604/60; 604/514

(58) Field of Classification Search ............ 604/60, 604/15, 57, 514, 48, 23, 12, 13, 14, 59, 91, 604/181, 275
See application file for complete search history.

(56) References Cited

U.S. PATENT DOCUMENTS

| | | | |
|---|---|---|---|
| 330,764 A | 11/1885 | Worley |
| 504,512 A | 9/1893 | Bailey |
| 2,281,600 A | 5/1942 | Ross |
| 2,290,571 A | 7/1942 | Peyton |
| 2,443,207 A | 6/1948 | Tedford |
| 2,532,598 A | 12/1950 | Boeger |
| 2,754,823 A | 7/1956 | Miller |
| 3,015,332 A | 1/1962 | Brecht |
| 3,139,886 A | 7/1964 | Tallman et al. |
| 3,220,413 A | 11/1965 | Sunnen |
| 3,667,465 A | 6/1972 | Voss |
| 3,835,856 A | 9/1974 | Warncke |
| 3,840,010 A | 10/1974 | Giglio |
| 4,248,229 A | 2/1981 | Miller |
| 4,341,211 A | 7/1982 | Kline |
| 4,341,221 A | 7/1982 | Testerman |
| 4,361,150 A | 11/1982 | Voss |
| 4,406,655 A | 9/1983 | Clayton |
| 4,421,504 A | 12/1983 | Kline |

(Continued)

FOREIGN PATENT DOCUMENTS

EP    1 040 808 A2    10/2000

(Continued)

OTHER PUBLICATIONS

Banerjee, S. et al., "Inflammatory Bowel Disease Medical Therapy of Specific Clinical Presentations," *Gastroenterol Clin N. Am*, 31: 185-202 (2002).

(Continued)

*Primary Examiner* — Kevin C Sirmons
*Assistant Examiner* — Imani Hayman
(74) *Attorney, Agent, or Firm* — Hamilton, Brook, Smith & Reynolds, P.C.

(57) ABSTRACT

Rectal suppositories are used to administer a predetermined drug dosage to treat a variety of diseases and symptoms in a variety of patient populations. Certain medical conditions, such as digestive disorders, may be more effectively treated when the suppository is placed in a particular location of the patient's anal canal or rectum. A method and apparatus for inserting a suppository into an animal or human may include an applicator having a barrel and plunger. The barrel maintains a first gas flow path during insertion of a suppository and the plunger maintains a second gas flow path during withdrawal of the plunger. By maintaining a first and second gas flow path, trapped air and suction effects on the suppository are minimized or eliminated. Furthermore, patients may immediately resume day-to-day activities. These benefits may encourage patients to maintain a course of treatment thereby potentially avoiding additional complications, hospitalization, and costs.

25 Claims, 15 Drawing Sheets

U.S. PATENT DOCUMENTS

| | | | |
|---|---|---|---|
| 4,752,288 | A | 6/1988 | Hussey |
| 4,990,136 | A | 2/1991 | Geria |
| 5,152,068 | A | 10/1992 | Meister et al. |
| D330,764 | S | 11/1992 | Lorentzon |
| 5,213,566 | A | 5/1993 | Weissenburger |
| 5,330,427 | A | 7/1994 | Weissenburger |
| 5,352,681 | A | 10/1994 | Wittebrood et al. |
| 5,354,325 | A | 10/1994 | Chive et al. |
| 5,460,617 | A | 10/1995 | Minkus et al. |
| 5,656,283 | A | 8/1997 | Brummer et al. |
| 5,662,601 | A | 9/1997 | Snead |
| 5,788,664 | A | 8/1998 | Scalise |
| 5,860,946 | A | 1/1999 | Hofstätter |
| 6,056,714 | A | 5/2000 | McNelis et al. |
| D436,661 | S | 1/2001 | Berry |
| 6,190,348 | B1 | 2/2001 | Tiemann et al. |
| 6,245,776 | B1 | 6/2001 | Skwierczynski et al. |
| 6,380,455 | B1 | 4/2002 | Moder et al. |
| 6,486,168 | B1 | 11/2002 | Skwierczynski et al. |
| 6,500,460 | B1 | 12/2002 | Bergeron et al. |
| D471,980 | S | 3/2003 | Caizza |
| 6,706,728 | B2 | 3/2004 | Hedenstrom et al. |
| 6,740,333 | B2 | 5/2004 | Beckett et al. |
| 6,786,883 | B2 | 9/2004 | Shippert |
| 7,070,581 | B2 | 7/2006 | Manera et al. |
| 7,081,110 | B2 | 7/2006 | Karapasha |
| 7,104,968 | B2 | 9/2006 | Swick |
| D529,603 | S | 10/2006 | Knickerbocker et al. |
| 7,122,025 | B1 | 10/2006 | Nestenborg |
| 7,149,574 | B2 | 12/2006 | Yun et al. |
| 7,192,607 | B2 | 3/2007 | Bergeron et al. |
| 7,198,612 | B2 | 4/2007 | Swick |
| 7,217,252 | B2 | 5/2007 | Swick |
| D572,362 | S | 7/2008 | Edgett et al. |
| D579,786 | S | 11/2008 | Py et al. |
| 7,465,295 | B2 | 12/2008 | Bergeron et al. |
| D585,988 | S | 2/2009 | Kinnard |
| 7,503,895 | B2 | 3/2009 | Rabiner et al. |
| 7,591,808 | B2 | 9/2009 | DiPiano et al. |
| D608,659 | S | 1/2010 | Py et al. |
| 7,666,160 | B2 | 2/2010 | Rajala et al. |
| 2002/0048601 | A1 | 4/2002 | Beckett et al. |
| 2002/0058674 | A1 | 5/2002 | Hedenstrom et al. |
| 2003/0045543 | A1 | 3/2003 | Hedenstrom et al. |
| 2003/0088217 | A1 | 5/2003 | Bergeron et al. |
| 2003/0233077 | A1 | 12/2003 | Swick |
| 2003/0233078 | A1 | 12/2003 | Swick |
| 2004/0047910 | A1 | 3/2004 | Beckett et al. |
| 2004/0249352 | A1 | 12/2004 | Swick |
| 2004/0249416 | A1 | 12/2004 | Yun et al. |
| 2004/0260252 | A1 | 12/2004 | DiPiano et al. |
| 2005/0004533 | A1 | 1/2005 | Smith |
| 2005/0021092 | A1 | 1/2005 | Yun et al. |
| 2005/0143378 | A1 | 6/2005 | Yun et al. |
| 2005/0143788 | A1 | 6/2005 | Yun et al. |
| 2005/0153885 | A1 | 7/2005 | Yun et al. |
| 2005/0240241 | A1 | 10/2005 | Yun et al. |
| 2005/0256028 | A1 | 11/2005 | Yun et al. |
| 2005/0273038 | A1 | 12/2005 | Osborn, III et al. |
| 2006/0034847 | A1 | 2/2006 | Yun et al. |
| 2006/0035974 | A1 | 2/2006 | Yun et al. |
| 2006/0069012 | A1 | 3/2006 | Yun et al. |
| 2006/0184100 | A1 | 8/2006 | Studin |
| 2006/0206149 | A1 | 9/2006 | Yun |
| 2007/0073267 | A1 | 3/2007 | Muller |
| 2007/0112327 | A1 | 5/2007 | Yun et al. |
| 2007/0129668 | A1 | 6/2007 | Swick |
| 2007/0185436 | A1 | 8/2007 | Swick |
| 2008/0038377 | A1 | 2/2008 | Citow |
| 2008/0097286 | A1 | 4/2008 | Cleator et al. |
| 2008/0161752 | A1 | 7/2008 | Rajala et al. |
| 2008/0167598 | A1 | 7/2008 | Gann et al. |
| 2008/0167599 | A1 | 7/2008 | Osborn et al. |
| 2008/0300575 | A1 | 12/2008 | Cleator et al. |
| 2008/0319269 | A1 | 12/2008 | Longo et al. |
| 2010/0010471 | A1 | 1/2010 | Ladd et al. |
| 2010/0145379 | A1 | 6/2010 | Isham |

FOREIGN PATENT DOCUMENTS

| | | | |
|---|---|---|---|
| EP | 1 319 420 | A1 | 6/2003 |
| EP | 1 530 978 | A1 | 5/2005 |
| WO | WO 2006/063377 | A1 | 6/2006 |
| WO | WO 2008/081353 | A1 | 7/2008 |
| WO | WO 2008/084453 | A1 | 7/2008 |
| WO | WO 2008/102341 | A2 | 8/2008 |

OTHER PUBLICATIONS

Bradshaw, A., "Rectal Suppository Insertion: The Reliability of the Evidence as a Basis for Nursing Practice," *Journal of Clinical Nursing*, 16: 98-103 (2006).

Expedited Review Request, Letter and Attachments A-C from Jennifer Davagian Ensign regarding Expedited Review of 510(k) Premarket Notification, Dated: Sep. 4, 2009.

Fernandez-Becker, N.Q. et al., "Improving Delivery of Aminosalicylates in Ulcerative Colitis," *Drugs*, 68(8): 1089-1103 (2008).

Hidaka, N. et al., "Changes in the Plasma Diazepam Concentration and Its Anticonvulsant Effect After the Discharge of a Diazepam Suppository from the Rectum in Rats," *Methods Find Exp Clin Pharmacol*, 29(6): 401-404 (2007).

Howell, H.R., "Ulcerative Colitis: Achieving and Maintaining Remission," *US Pharm*, 33(12): 30-37 (2008).

Regueiro, M. et al., "Medical Management of Left-Sided Ulcerative Colitis and Ulcerative Proctitis: Critical Evaluation of Therapeutic Trials," *Inflamm Bowel Dis*, 12(10): 979-994 (Oct. 2006).

Tindall, W.N. et al., "Mild-to-Moderate Ulcerative Colitis: Your Role in Patient Compliance and Health Care Costs," *Supplement to Journal of Managed Care Pharmacy*, 13(7, S-a): S2-S15 (with attached 2 page Evaluation) (Sep. 2007).

Notification of Transmittal of International Search Report and Written Opinion of the International Searching Authority, dated Jun. 16, 2010.

Amendment Under Article 34 and Reply to Written Opinion filed in corresponding Application No. PCT/US2009/059623, via Express Mail on Sep. 16, 2010.

Notification of Transmittal of International Preliminary Report on Patentability, dated Mar. 28, 2011, for Application No. PCT/US09/59623, consisting of 5 pages.

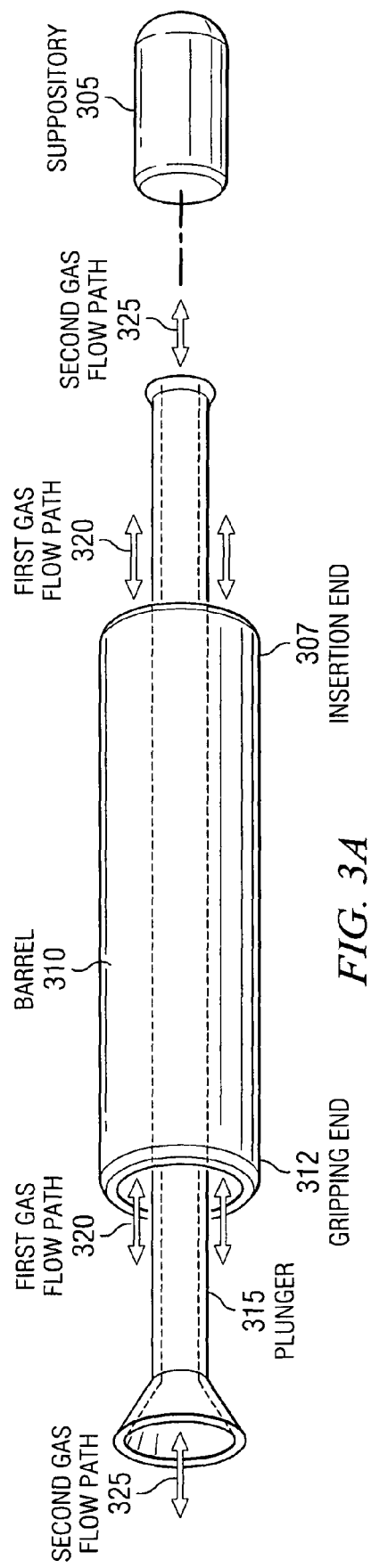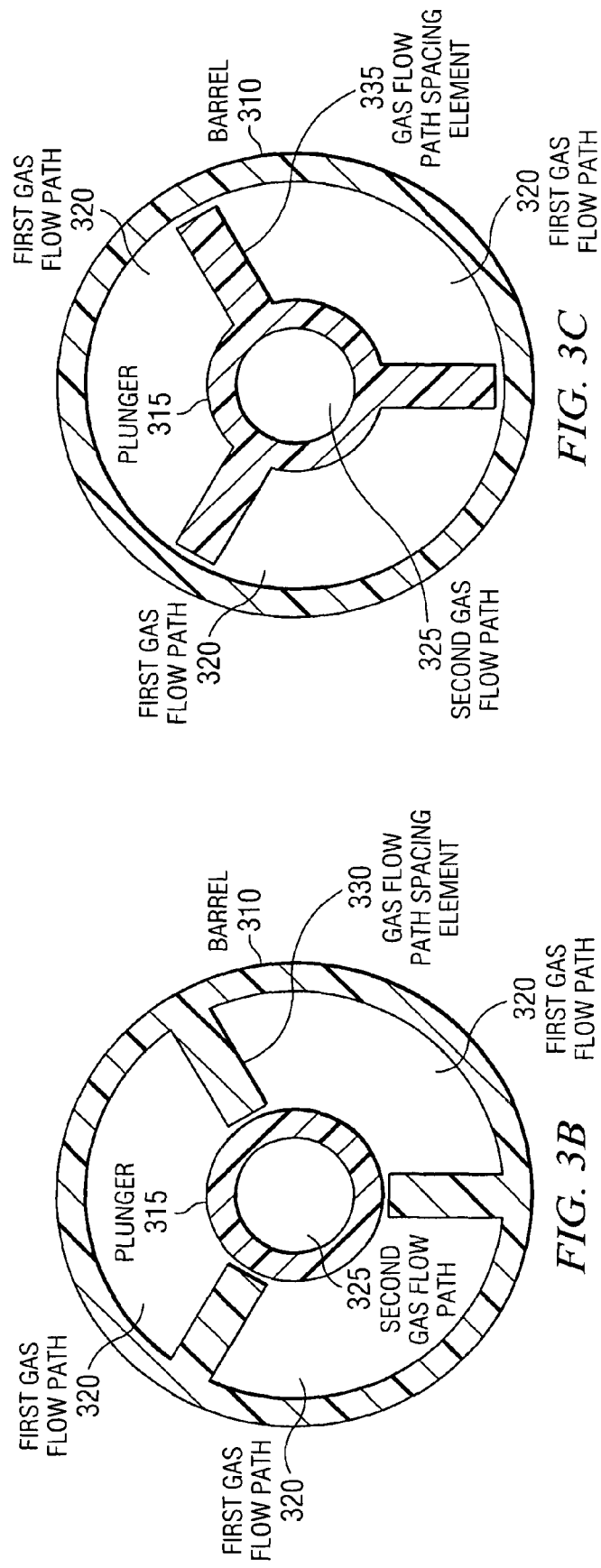

METHOD AND APPARATUS FOR INSERTING A RECTAL SUPPOSITORY

BACKGROUND OF THE INVENTION

Rectal suppositories are used to administer a predetermined drug dosage to treat a variety of diseases and symptoms. Rectal suppositories are designed to melt inside the body allowing the drug dosage contained within the rectal suppository to be absorbed by the mucosa lining of the rectum in order to treat a patient locally or systemically. Suppositories are typically used to administer drugs to patients who cannot take the drug orally for a variety of reasons, such as uncontrollable vomiting or nausea, chronic illnesses, and gastrointestinal diseases. In addition, children, the elderly, and patients unable to care for themselves may also use rectal suppositories to treat a variety of symptoms and conditions. In other cases, specific drugs can cause extreme stomach upset or are inactivated in the stomach or liver and are, therefore, better tolerated by rectal administration.

It is common practice to administer rectal suppositories manually using a finger while the patient is, for example, lying on their left side in the fetal position, and after having emptied their bowel. After insertion of the suppository, the patient is instructed to remain on their side in the fetal position for an extended period of time (e.g., at least 30 minutes) while the suppository has time to melt within the rectum and the body begins the absorption process.

SUMMARY OF THE INVENTION

An apparatus and corresponding method for inserting a rectal suppository into an animal or human according to example embodiments includes a barrel configured to be inserted into an anal canal, the barrel having ends defining at least one first gas flow path into and out of the body. The example embodiment further includes a plunger defining at least one second gas flow path into and out of the body and is configured to be movably coupled to the barrel with the at least one first gas flow path maintained. The plunger is movably extendable past an open end of the barrel to insert a suppository into the rectum while maintaining the at least one first gas flow path during a state of insertion of the suppository into the rectum. The at least one second gas flow path is maintained during withdrawal of the plunger away from the suppository.

Alternative example embodiments may further include an insertion end of the plunger that is configured to insert the suppository above an "anal trigger zone" into the rectum to minimize contact of the suppository or its medication with nerves that trigger contraction of anal sphincter muscles that may affect the body's ability to retain and absorb the medication.

Other example embodiments may further include at least one gas flow path spacing element configured to maintain the at least one first gas flow path with the plunger movably coupled to the barrel. The barrel may include the at least one gas flow path spacing element, the at least one gas flow path spacing element extending inward from an inner wall of the barrel while maintaining the at least one first gas flow path defined by the barrel to contact an outer wall of the plunger. Alternatively, the plunger may include the at least one gas flow path spacing element, the at least one gas flow path spacing element extending outward from an outer wall of the plunger while maintaining the at least one first gas flow path defined by the barrel to contact an inner wall of the barrel.

In another example embodiment, the barrel can include at least one gas flow path spacing element extending inward while maintaining the at least one first gas flow path defined by the barrel and wherein the plunger includes at least one gas flow path spacing element extending outward while maintaining the at least one first gas flow path. Alternatively, the embodiment may include at least two gas flow path spacing elements, defined by at least one gas flow path spacing element extending inward from the barrel and at least one gas flow path spacing element extending outward from the plunger, wherein the at least two gas flow path spacing elements are configured to interconnect in a movable relationship to each other.

According to other example embodiments, the barrel and the plunger may be shaped to provide at least one gas flow path between each other with the plunger positioned at least partially within the barrel. The barrel may include at least two subbarrels arrangeable to form the barrel and the plunger may include at least two subplungers arrangeable to form the plunger.

In yet another example embodiment, the barrel and the plunger each defines a hollow tube. The barrel may include an inner wall that defines a hollow tube and further includes an outer wall coupled to the inner wall by a structure to define the at least one first gas flow path. Conversely, the plunger may define a non-hollow structure and at least one gas flow path spacing element extending outward from a wall of the structure is configured to press on tissue between the anal canal or rectum and the plunger in a manner defining the at least one second gas flow path.

Some example embodiments may include a suppository support element configured to support a suppository at least partially below an open end of the barrel. The plunger may include a suppository interface end that is as wide or wider than a portion of the suppository with which the interface end is configured to contact. Alternatively, the plunger includes a suppository interface end that is narrower than a portion of the suppository with which the interface end is configured to contact.

In accordance with another example embodiment, the plunger has an insertion end and a hand or finger-interface end where the plunger has a length that enables a user self-administering the suppository to push the plunger with their palm or finger tip against the hand or finger-interface end. Note that the barrel or plunger may be formed from plastic, polycarbonate, epoxy, acrylic, silicon, rubber, polymer, ceramic, metal, cardboard, glass, wood, paper, or similar such materials.

Alternative example embodiments for inserting a suppository into an animal or human may include a barrel configured to insert into an anal canal and a plunger defining at least one gas flow path and is further configured to be coupled to the barrel with the at least one gas flow path maintained. The plunger is extendable past an open end of the barrel to insert a suppository into the anal canal or rectum while maintaining the at least one gas flow path during a state of withdrawal of the plunger away from the suppository. The plunger may be fixedly coupled to the barrel. Alternatively, the plunger may be movably coupled to the barrel. The plunger may be further configured to insert the suppository into the rectum.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-C are illustrations of applicators configured to insert a rectal suppository according to example embodiments of the invention;

DETAILED DESCRIPTION OF THE INVENTION

A description of example embodiments of the invention follows.

The effect of many drugs administered orally may be reduced or inactivated in the stomach because of the acidic and/or enzymatic content of the stomach or the drug may be subject to digestive attack and/or to microbial degradation. Oral administration of drugs also directs the absorbed substances through the liver where the drug's effectiveness can be further reduced or inactivated. As a result, rectal suppositories are often the most effective mode of delivery for the administration of a variety of drugs associated with medical conditions.

Rectal suppositories are composed of active pharmacological ingredients and an inactive binding agent that maintains the drug in a desired shape and stable form prior to, and during, insertion into the rectum. The inactive binding agents are designed so that the suppositories remain stable at or below room temperature. At or above body temperature, suppositories are designed to melt or dissolve so that the encapsulated medication may be released for absorption by the patient. Suppositories are formed to ease insertion and are commonly manufactured to maintain a round or bullet shaped appearance.

Drugs administered via rectal suppositories are intended to obtain a local therapeutic effect or systemic therapeutic effect. The effective ingredient in the medicine administrated by rectal application is often intended to be directly absorbed in the venous plexus of the rectum to be distributed throughout the body by the blood circulation without passing the portal vein and the liver. Therefore, a rectally applicable medicament form is preferable particularly for the medicines for which the effective ingredient causes a disorder in the stomach when orally administrated or the ingredient is susceptible to decomposition in the digestive tract or liver resulting in decreased effectiveness of the medicine.

The effectiveness and convenience of a number of drugs administered via rectal suppository form can be improved if positioned in a particular region of the anal canal or rectum. For example, rectal suppositories used for the treatment of hemorrhoids may be positioned relatively shallow. On the other hand, certain types of drugs, such as those used for digestive disorders, may be inserted relatively deeper, that is, further up the anal canal or into the rectum, to ensure sufficient absorption, to treat a greater portion of the gastro-intestinal tract, and to prevent leakage of the drug out of the body.

Figure 1A:
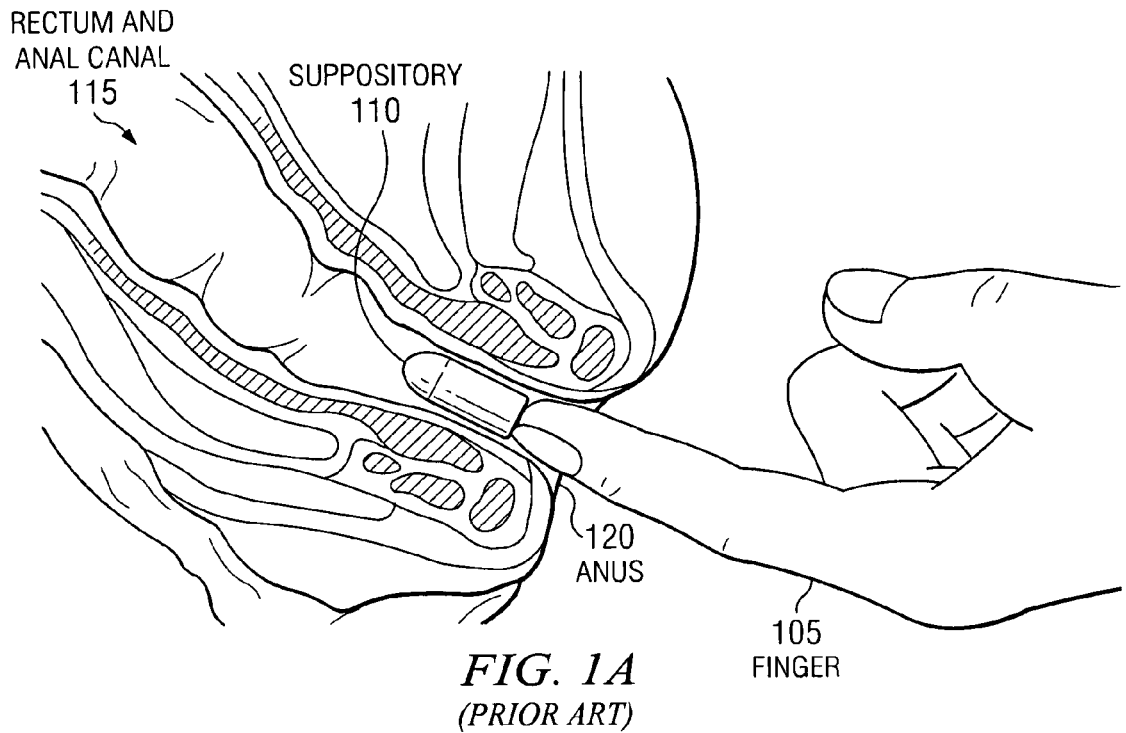
FIGS. 1A-B illustrate known techniques for inserting a rectal suppository.

FIG. 1A illustrates a known technique for inserting a suppository 110 by using a finger 105 to manually insert the suppository into a body cavity, such as a rectum or anal canal 115. To use this technique, it is necessary to wash hands thoroughly prior to insertion, or alternatively, enclose the finger 105 or hand with a sanitized latex covering or the like. The patient or medical personnel aligns one end the suppository 110 with the patient's anus 120. After the suppository 110 is properly aligned, the finger 105 is used to push the suppository 110 into an optimal position in the rectum or anal canal 115 and the finger 105 is removed. Once in place, the patient's body heat will begin to melt the suppository 110 releasing the encapsulated medication so that the drug can began to be absorbed within the patient's rectum or anal canal 115.

However, when used with rectal suppositories, the finger insertion technique suffers from a number of disadvantages that significantly impact convenience and drug absorption. First, when the finger 105 is withdrawn from the rectum or anal canal 115, a pocket of air is created and remains in the rectum or anal canal 115 as trapped gas. The trapped gas will eventually be released as flatulence. Along with the passage of gas, a portion of the suppository 110 that has melted due to body temperature, but not yet absorbed by the mucosa lining of the rectum, is expelled from the body, staining the patient's clothing. To prevent ruining clothing and embarrassing accidents, many patients resort to wearing sanitary pads and undergarments. The released gas may also be embarrassing for the patient in social situations. Second, withdrawal of the finger 105 also creates a suction effect that draws the suppository 110 out of the intended position, moving the suppository 110 toward the opening of the rectum or anal canal 115. This movement further increases the likelihood of drug leakage and/or expulsion. Third, certain drugs, such as those for digestive disorders, have an optimal placement position deeper than that which is obtainable using this or other known techniques due to, for example, limited finger 105 length or body mechanics in the case of self administration. Because the suppository 110 is placed in a shallower position than optimal, the potential for leakage and/or expulsion is further increased thereby reducing the amount of medication that is absorbed by the body. In addition, shallow placement may also stimulate internal sphincter muscles creating a sensation in the patient indicative of a need to empty their bowel. Fourth, the inner wall of the rectum or anal canal 115 is easily scratched and injured by the finger's 105 fingernail resulting in potential injury and/or pain. If used with a latex glove or finger wrap, the latex may tear and can cause irritation in some patients.

Figure 1B:
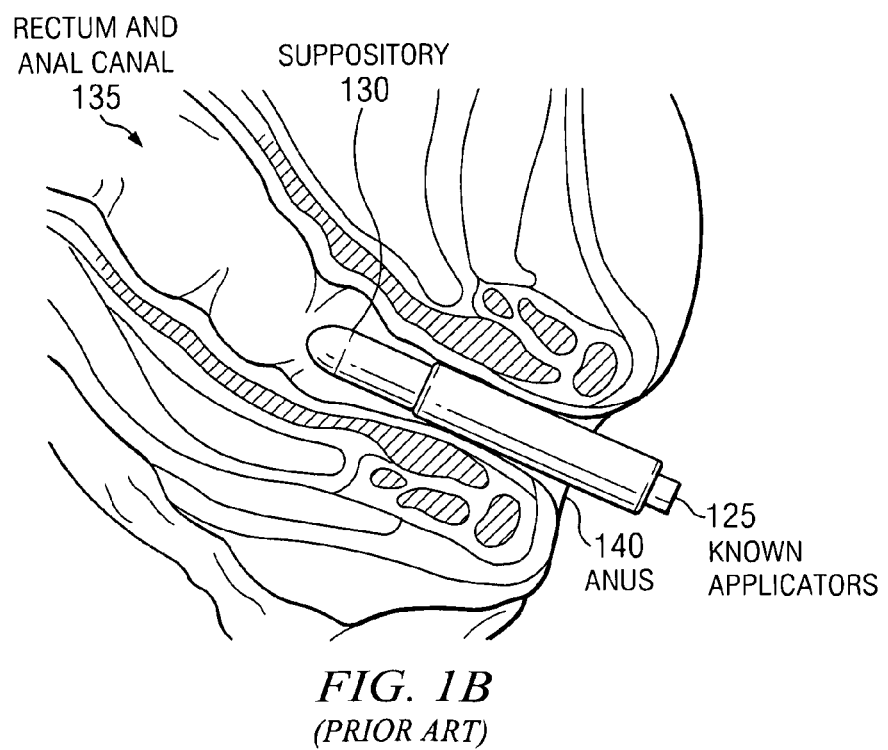

FIG. 1B illustrates another technique for inserting a rectal suppository 130 include the use of various known applicators 125. Such applicators 125 are more hygienic and can aid in the ergonomic difficulties of self administration. These applicators 125 are typically modified versions of vaginal applicators used for shallow placement of objects, such as tampons or medicated creams, into the vaginal canal. As such, these applicators 125 are designed to accommodate anatomical features of the vagina rather than the anal canal and rectum 135. The smooth, flat muscles of the vagina walls do not subconsciously and spontaneously contract. Furthermore, vaginal-type applicators 125 are not intended to insert objects beyond the relatively shallow depth of the vagina. Consequently, due to the anatomical characteristics of the vagina, vaginal applicators 125 used to insert objects into the vagina do not create the air pocket or the suction problems described above.

However, when vaginal-type applicators 125 are used to insert suppositories 130 into the rectum or anal canal 135, many of the same disadvantages associated with finger insertion are exhibited. For example, as the applicator 125 is inserted and then withdrawn from the rectum or anal canal 135, a pocket of air is created and remains in the body as trapped gas where it will eventually be released as flatulence. The passage of gas causes medication not yet absorbed in the rectum to be expelled along with the gas. In addition, withdrawal of the applicator 125 also creates a suction effect that draws the suppository 130 out of an optimal placement position, moving the suppository 130 out toward the anus 140, increasing the likelihood of drug leakage and/or suppository expulsion. Furthermore, vaginal-type applicators are designed for shallow placement of objects (e.g., approximately 4 to 6 centimeters (cm)) and, as a result, cannot optimally position suppositories 130 in which deeper placement is desired.

To mitigate some of the disadvantages associated with inserting a rectal suppository using a finger or known applicators, patients are often instructed to empty their bowel before inserting a suppository. The suppository is then inserted into the patient using the finger insertion technique or known applicators. After the suppository has been inserted, patients are instructed to remain on their left side in the fetal position for at least 30 minutes. In doing so, as a suppository melts and the drug is released, the horizontal position reduces potential leakage as a result of the aforementioned disadvantages. In addition, the user may also be instructed to wear protective hygiene products to protect garments from any medication that is expelled.

Figure 2:
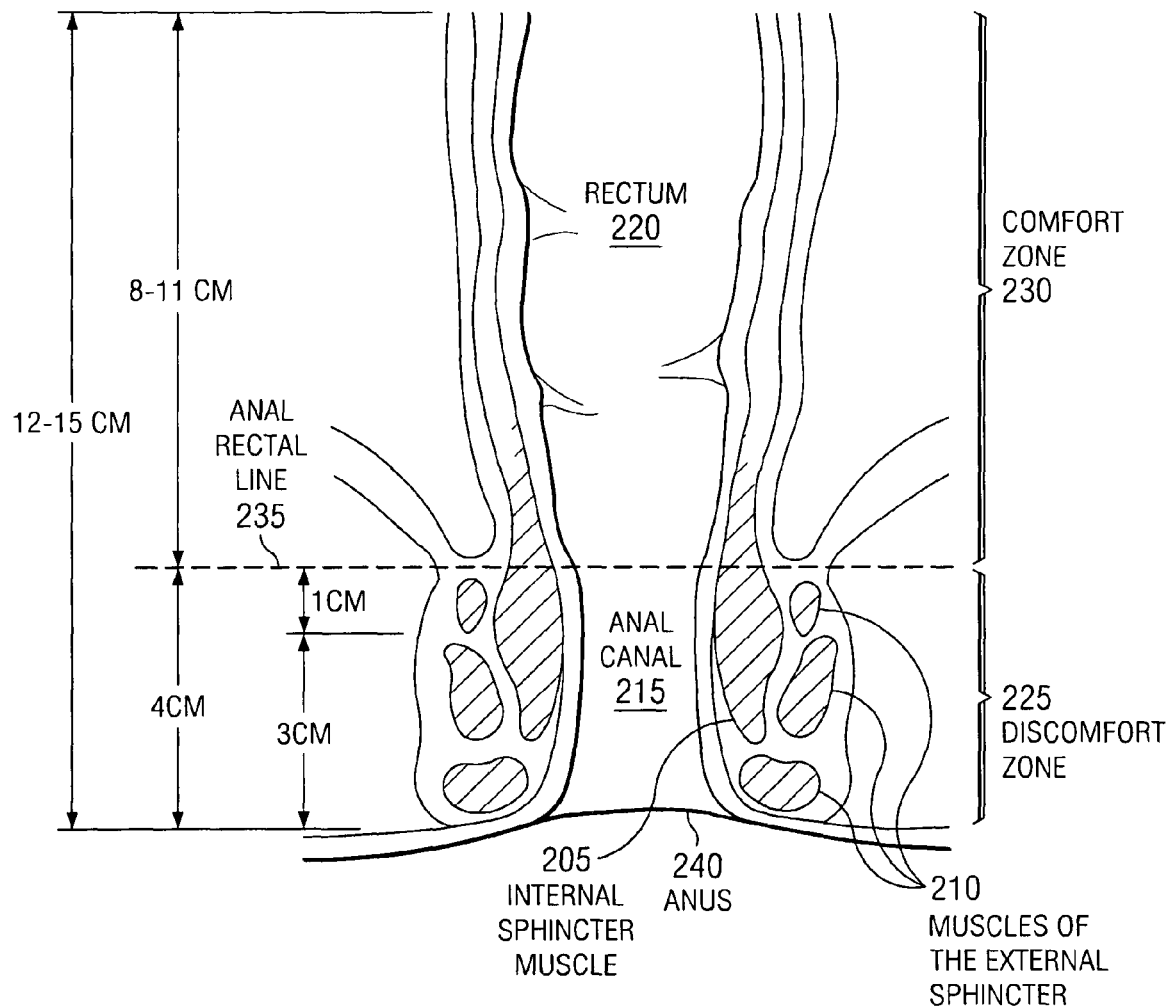
FIG. 2 is an anatomical diagram of a human rectum and anus.

The contrasting effects that occur when vaginal-type applicators are used to insert rectal suppositories in the rectum are due to anatomical differences between the vagina and anal canal. Referring to FIG. 2, the sphincter muscles 205, 210 are circular bands of muscles surrounding the anal canal 215 that consciously and subconsciously contract and relax to control the movement and passage of material through and out of the gastrointestinal tract. Upon reaching the rectum 220, fecal matter is held inside the body by the sphincter muscles 205, 210 until it is convenient to expel the contents of the rectum and anal canal. In contrast, the muscles of the vagina are smooth and flat, and because they do not need to move bulk material through the vagina, they do not subconsciously and spontaneously contract and relax. The vagina lacks the ability to control and prevent the movement and expulsion of material, such as, for example, menstrual flow. Because of this, the formation of air pockets and suction effects described above do not occur in the vagina.

Because the anal canal 215 and the rectum 220 are relatively long (e.g., 10 to 15 cm) as compared with the vaginal canal (e.g., 4 to 6 cm), vaginal-type applicators are not capable of inserting suppositories in the rectum 220 at optimal depths. Certain types of rectal suppositories are more effective, convenient, and comfortable when placed further up the rectum, for example, above the "discomfort zone" 225. As used herein, the discomfort zone 225 refers to an approximately 4 cm section of the anatomy closest to the anus 240, known as the anal canal. This is the section below the anal-rectal demarcation line 235 where a patient's sphincter muscles reside. It is here that fecal matter or other material (e.g., suppository) stimulates the internal sphincter muscles 205 creating a sensation indicating that the bowels need to be emptied. The discomfort zone 225 is also referred to as an "anal trigger zone" and may be used interchangeably herein. The "comfort zone" 230 as used herein refers to a section of the rectum 220 above the discomfort zone 225, that is, a section of the rectum located between approximately 4 cm and 15 cm from the anus 240.

Suppositories positioned within the discomfort zone may stimulate the sphincter muscles 205, 210 causing the urge to defecate, and should a patient do so, all or part of the medication may be expelled along with any fecal matter, reducing the amount of medication available for absorption by the body. Suppositories positioned above the discomfort zone 225, that is, within or above the comfort zone 230, reduce or eliminate the urge to defecate due to stimulation of the sphincter muscles. Additional benefits include less leakage, less likelihood of expulsion, and increased absorption. Increased insertion depth also significantly improves patient convenience by eliminating the 30 minutes patients must currently remain on their side (i.e. horizontal) to ensure adequate absorption. This allows the patient to immediately resume normal day-to-day activities.

It should be noted that although the above anatomical discussions refer to female anatomy, the present invention is by no means limited to females only and example embodiments of the present invention are equally suitable for use with males and females.

FIG. 3A illustrates an example embodiment of an applicator configured to insert a rectal suppository 305 into a human or animal according to the present invention. The applicator may include a barrel 310 and a plunger 315. The barrel 310 has a gripping end 312 and an insertion end 307 and is appropriately sized and shaped to fit within a patient's anal canal. The barrel 310 is further configured to define a gas flow path 320 allowing gas to freely flow through the barrel 310 when positioned within the anal canal. The plunger 315 is configured to be substantially longer than the barrel, thereby allowing the plunger 315 to extend beyond the end of the barrel 310. For example, the barrel 310 may be approximately 4 cm whereas the plunger may be approximately 8 cm.

Thus, the applicator can be configured to insert a suppository 305 above a patient's anal trigger zone. In doing so, the suppository 305 minimizes contact with nerves that trigger the anal muscles that may effect (i.e., reduce) the body's ability to retain and absorb medication provided by the suppository. For example, when a suppository is positioned within the anal trigger zone excessive contact with these nerves may create the urge to release contents within the bowel and, along with these contents, a portion of medication that has been released from the suppository but not yet absorbed by the body. It should be noted that the aforementioned dimensions are merely examples and are not meant to be limiting and alternative dimensions may be similarly used such that the plunger 315 extends beyond the barrel 310.

The plunger 315 may be configured to be movably or slidably coupled to the barrel 310 and is further configured to maintain a second gas flow path 325 that allows gas to freely flow through the plunger 315 as the plunger is withdrawn from the rectum and anal canal after the suppository 305 has been inserted to a desired position. Thus, as the suppository 305 is being inserted, the barrel 310 maintains a gas flow path 320 allowing gas to escape. As the plunger 315 is being withdrawn, the plunger's gas flow path 325 and the barrel's gas flow path 320 are maintained as the plunger is withdrawn from the suppository 305 and the barrel 310 and plunger 315 are removed from the patient's anal canal. The gas flow paths, 325 and 320 allow gas to escape as the barrel 310 and the plunger 315 are removed from the body preventing or reducing the need to release the gas in the form of flatulence.

FIGS. 3B and 3C illustrate end views of an applicator that further includes at least one gas flow path spacing element 330, 335 configured to maintain the barrel's 310 gas flow path 320. Referring to FIG. 3B, the barrel 310 includes the at least one gas flow path spacing element 330 where the spacing element extends inward from an inner wall of the barrel 310 to contact the outer wall of the plunger 315, thereby maintaining barrel's gas flow path 320. Since the plunger 315 is hollow, a second gas flow path 325 is maintained within the plunger 315 as well. FIG. 3C illustrates an alternative example embodiment where the at least one gas flow path spacing element 335 extends outward from an outer wall of the plunger 315 to contact an inner wall of the barrel 310 to maintain the barrel's gas flow path 320. Also shown is the at least one second gas flow path 325 maintained by a similarly hollow plunger 315. Alternatively, at least two gas flow path spacing elements may simultaneously extend inward from the inner surface of the barrel 310 and outward from the outer surface of the plunger 315 to maintain the first gas flow path 320.

Figure 4A:
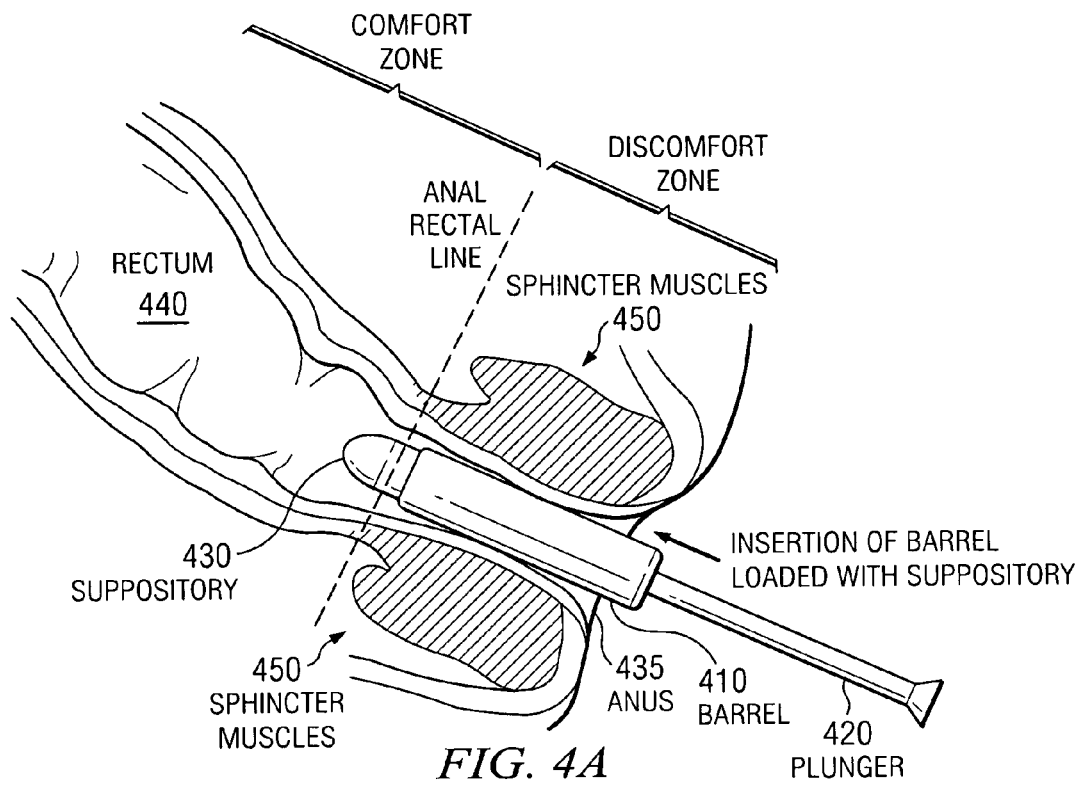
FIGS. 4A-C are anatomical diagrams illustrating an example embodiment of the invention in various states of use.
Figure 4B:
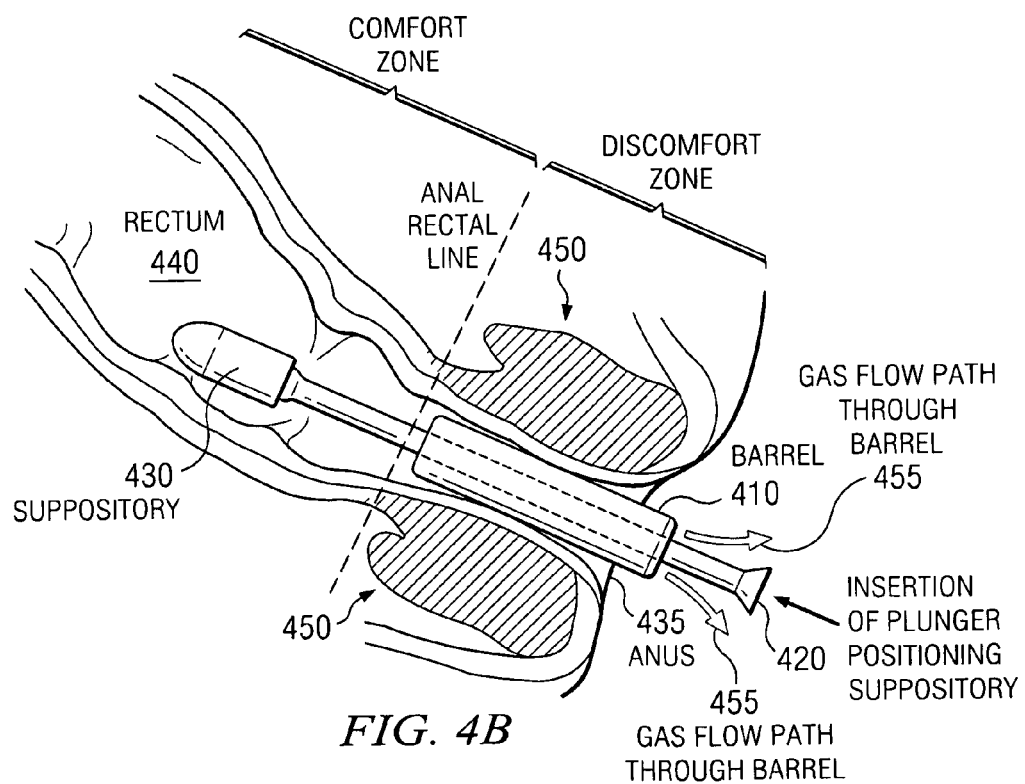
Figure 4C:
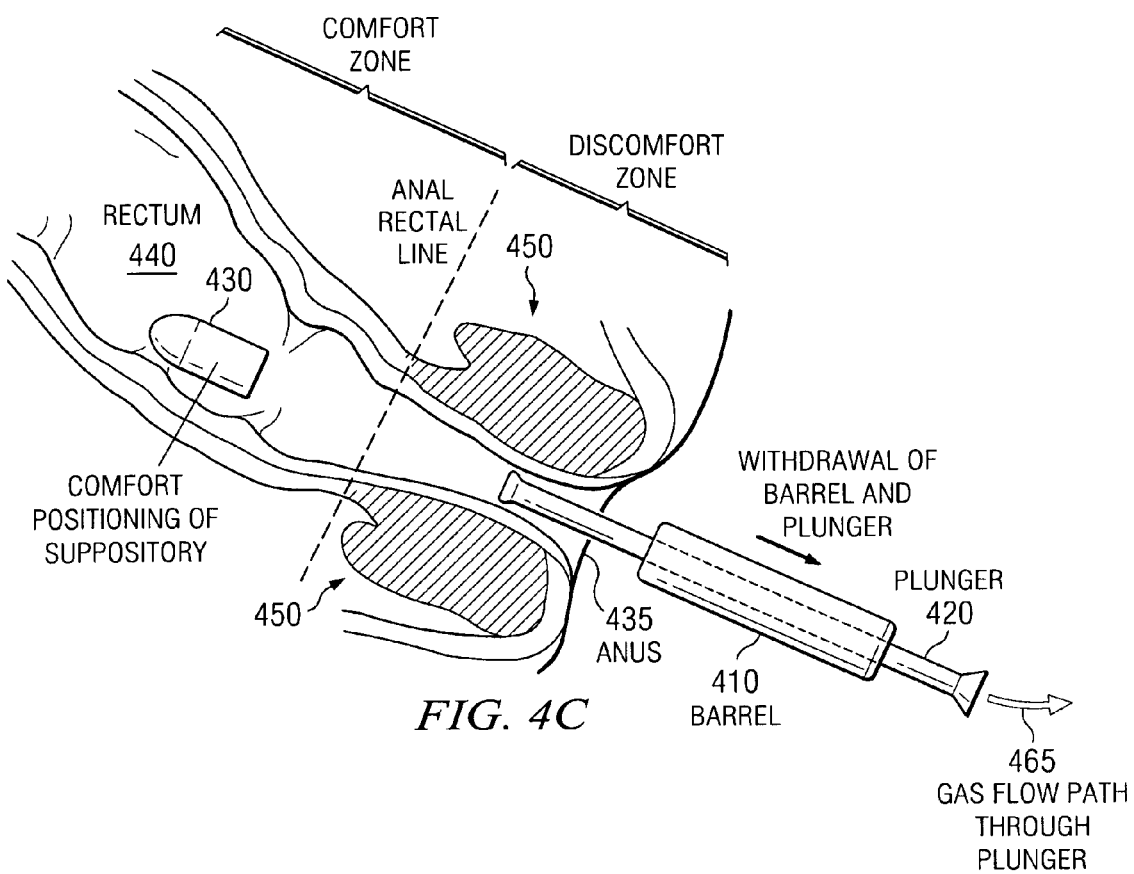

FIGS. 4A-C illustrate an example embodiment employing an applicator to insert a suppository 430 into a patient's rectum 440 in varying states of use. The applicator may include a barrel 410 and a plunger 420. Referring to FIG. 4A, the plunger 420 is positioned within the barrel and the suppository 430 is loaded into the barrel 410. The applicator is then inserted into the patient's anus 435. Referring to FIG. 4B, the plunger is depressed such that the suppository 430 is inserted within the rectum 440 to a desired position, such as a location within a comfort zone above the patient's sphincter muscles 450 (i.e., above an anal trigger zone). As the plunger 420 is inserted or pushed into the barrel, the barrel 410 maintains a first gas flow 455 such that any trapped air may escape through the barrel 410 to outside the patient's anus 435. Referring now to FIG. 4C, once the suppository has been positioned in the desired location, the applicator may be removed from the patient's rectum 440. As the plunger 420 is removed, suction effects due to withdrawal of the plunger 420 are prevented by venting any pressure or vacuum buildup through the second gas flow path 465 maintained by the plunger 420.

Figure 4E:
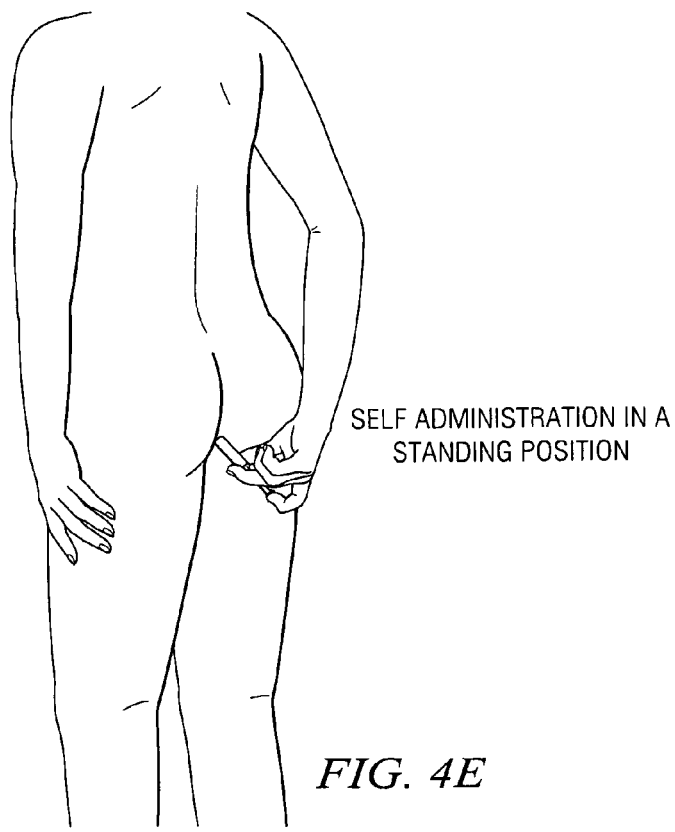
FIG. 4E illustrates inserting a rectal suppository in a standing position according to an example embodiment.
Figure 4D:
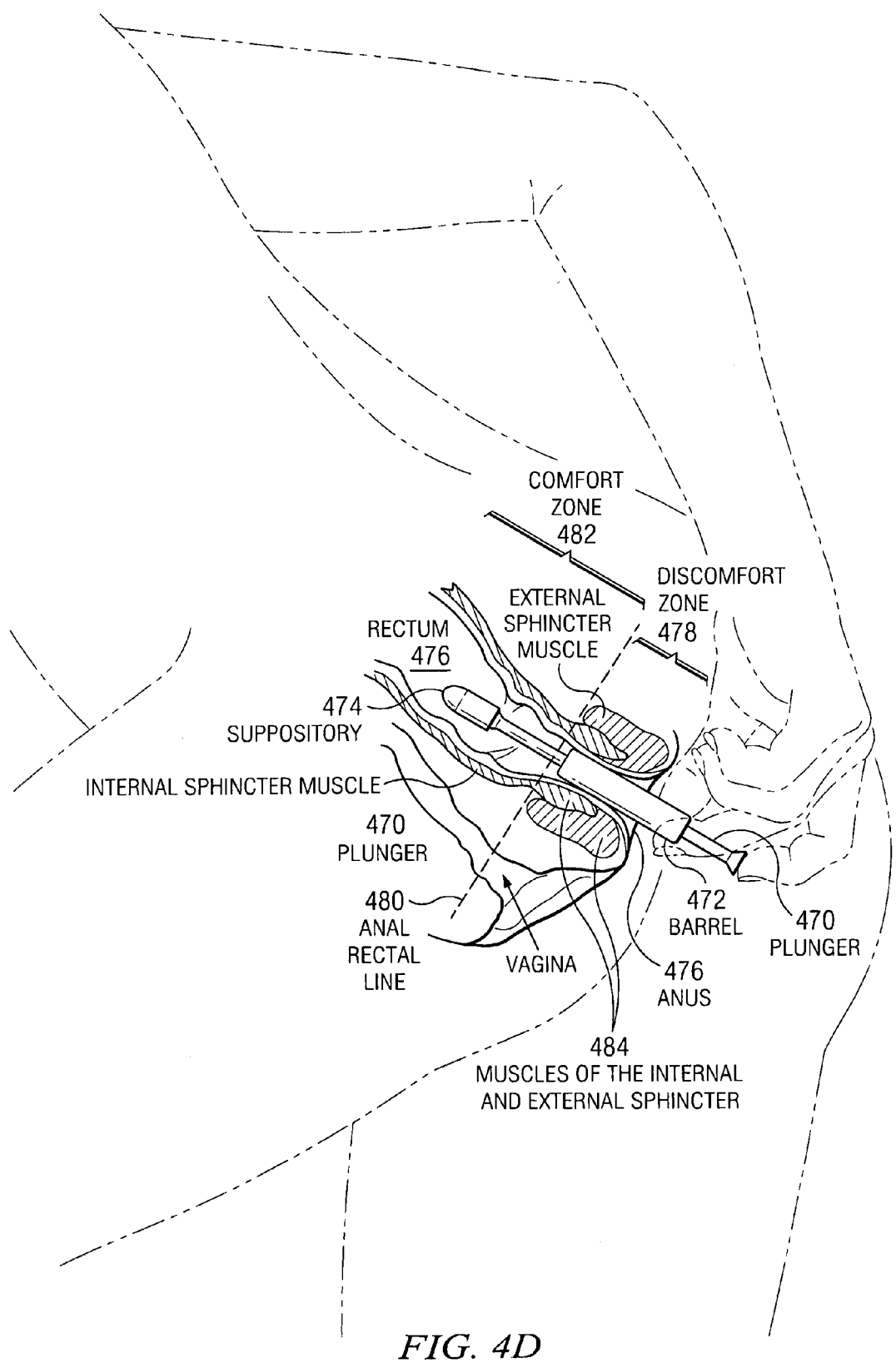
FIG. 4D is a larger perspective anatomical diagram illustrating an example embodiment of the invention.

FIG. 4D is a larger perspective anatomical diagram illustrating a patient employing an applicator to self-administer a rectal suppository according to an example embodiment of the invention. The applicator may include a plunger 470 and barrel 472 configured to insert a suppository 474 into a patient's rectum 476. The barrel 472, plunger 470, and suppository 474, are positioned at the patient's anus 476 and then inserted into the patient. The barrel 472 typically does not extend beyond the anal-rectal line 480, that is, remains within the discomfort zone 478, although the example embodiment is not limited as such and the barrel 472 may extend into the patient's comfort zone 482. Once the applicator has been positioned properly, the patient may depress the plunger 470 to cause the suppository 474 to be placed in a desired position, such as an area within the comfort zone 482 of the rectum 476. As the user withdraws the applicator, trapped air or suction effects may be vented via a first or second gas flow path maintained by the barrel 472 or plunger 470, respectively.

As a result, the applicator may be used to mitigate the ergonomic difficulties presented when self-administering rectal suppositories. The applicator also reduces trapped gas and suppository 474 movement upon insertion and withdrawal, and reduces leakage or expulsion due to stimulation of the sphincter muscles 484. In addition, placement within the patient's comfort zone 482 may also allow the patient to resume their day-to-day activities almost immediately (rather than remaining in a horizontal position until the suppository has dissolved and medication has been absorbed). Consequently, patients may be more likely to continue their prescribed treatment course allowing the patient to obtain full benefit of the suppository's medication. This may result in reduced complications, hospitalization, and/or placing a patient on a stronger drug regime due to noncompliance. Thus, effective delivery of rectal suppositories provided by example embodiment of the present invention may improve patient health and well-being. It should be noted that the above description equally applies when, for example, another person, such as healthcare personnel employs the applicator to insert a suppository into a patient or animal.

FIG. 4E illustrates a method for inserting a rectal suppository in a standing position according to an example embodiment of the present invention. Self-administration of rectal suppositories can be especially challenging due to the body mechanics required to adequately align, position, and insert the suppository as well as a reduced line of sight toward an insertion point. Body mechanics and line of sight issues make self-administration even more difficult when the patient is in a standing position. Consequently, self-administration while in a standing position is often not a viable option for many patients. However, employing an applicator according to the present invention enables a patient to overcome these issues by providing increased depth positioning ability and control. Thus, a patient can use the applicator of the present invention to self-administer a rectal suppository while in a number of different positions including standing, squatting, sitting, prone, fetal, or other positions.

The example embodiments illustrated in FIGS. 3A-C and 4A-C are examples of a plunger and barrel configured to maintain a first and second gas flow path. However, numerous other barrel and plunger configurations are envisioned where a first and second gas flow path are maintained within the barrel and plunger, respectively.

Figure 5A:
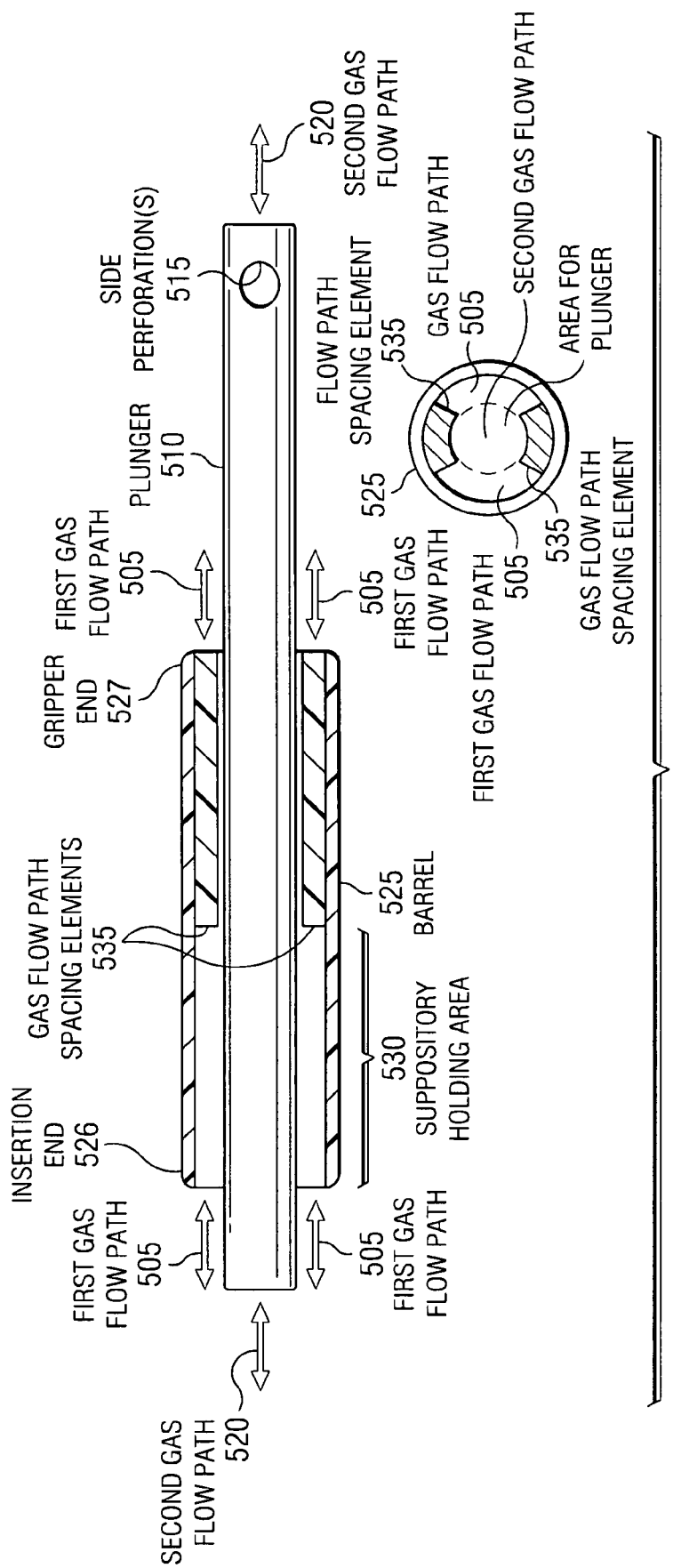
FIGS. 5A-B illustrate alternative example embodiments of the invention.

For example, FIG. 5A illustrates an example embodiment where a barrel maintains a first gas flow path 505 and a plunger 510 having side perforations 515 configured to maintain or augment at least one second gas flow 520. Gas flow path spacing elements 535 may extend inward from the barrel 525 to contact the plunger 510. Gas flow path spacing elements 535 may be configured to provide a suppository holding area 530 during insertion of the apparatus into the anal canal. Alternatively, or in addition, the gas flow path spacing elements 535 may extend from the outer surface of the plunger 510 to contact the inner surface of the barrel 525.

Figure 5B:
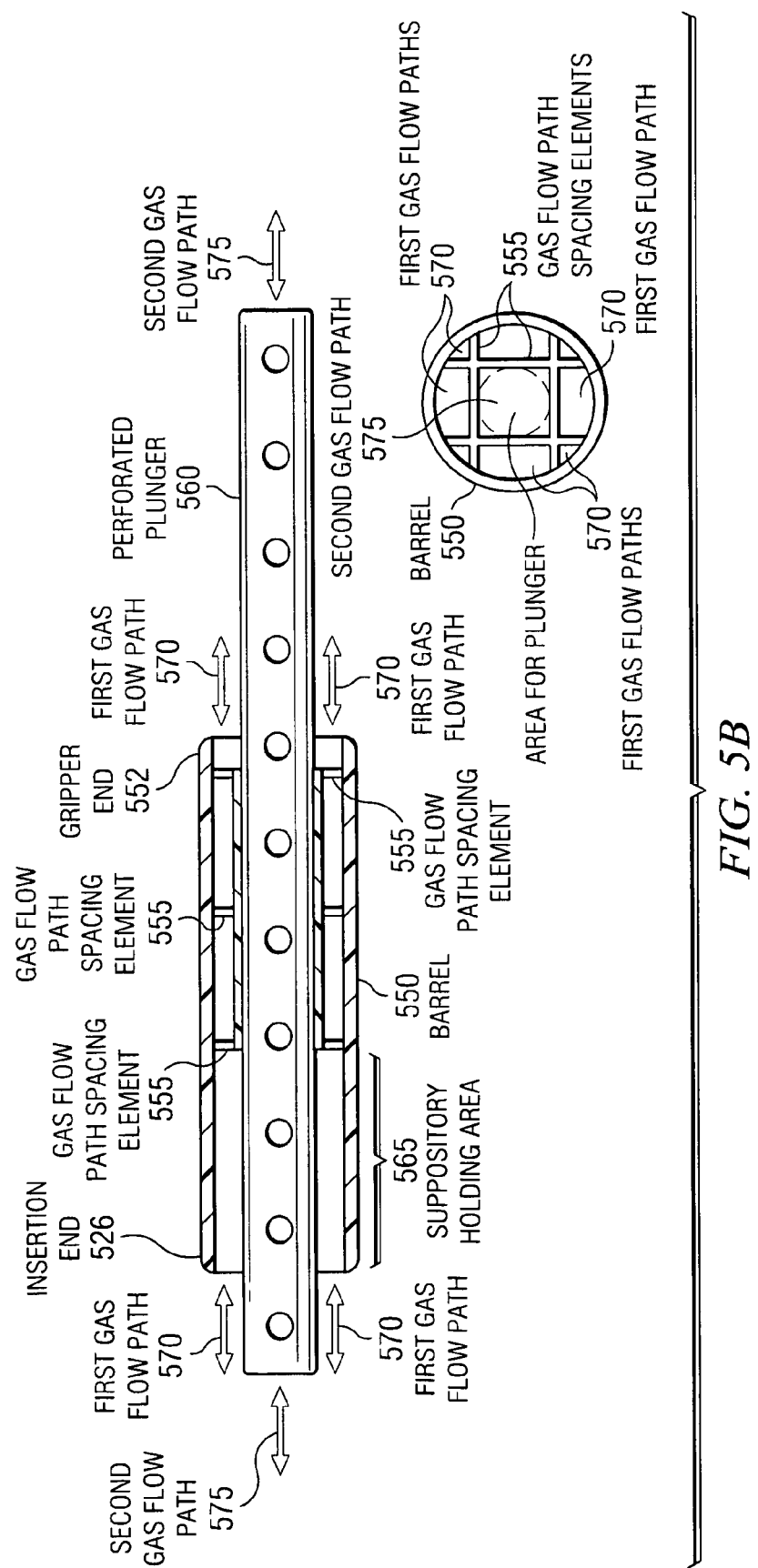

FIG. 5B illustrates another example embodiment depicting a barrel 550 that includes gas flow path spacing elements 555 configured in a horizontal and vertical arrangement to maintain the first gas flow path 570. In addition, the plunger 560 includes multiple perforations in order to maintain or augment the second gas flow path 575 maintained by the plunger 560. Alternatively, the plunger 560 may be replaced with a solid (i.e., non-hollow) plunger where the gas flow path spacing elements extend outward from the plunger to press on tissue between the anal canal or rectum and the plunger. In this manner, the second gas flow path is maintained in the space created between the solid plunger and the anal canal or rectum.

Note that the gas flow path spacing elements 535, 555 in FIGS. 5A and 5B may extend from a gripper end 527, 552 of the barrel 525, 550 to a point before the insertion end 526, 551 such that the absence of the gas flow path spacing elements 535, 555 can support a suppository partially or completely below an open end of the barrel's insertion end. This feature allows the user to place the suppository into a holding area 530, 565 at the insertion end of the barrel 525, 550 to support the suppository prior to and during insertion of the applicator.

Figure 6A:
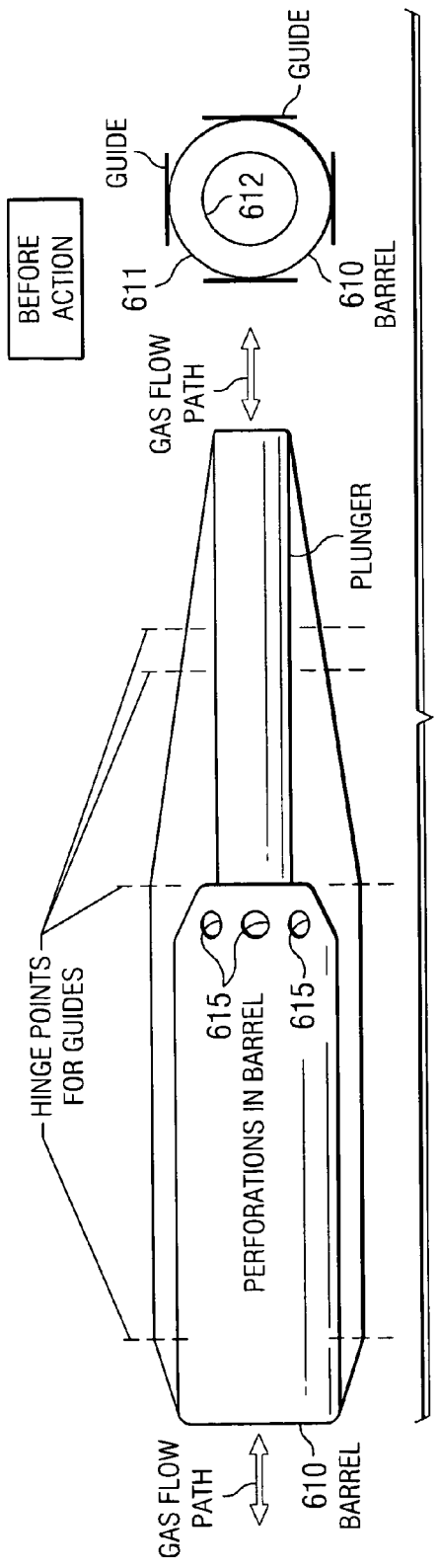
FIGS. 6A-C illustrate additional alternative example embodiments of the invention.
Figure 6B:
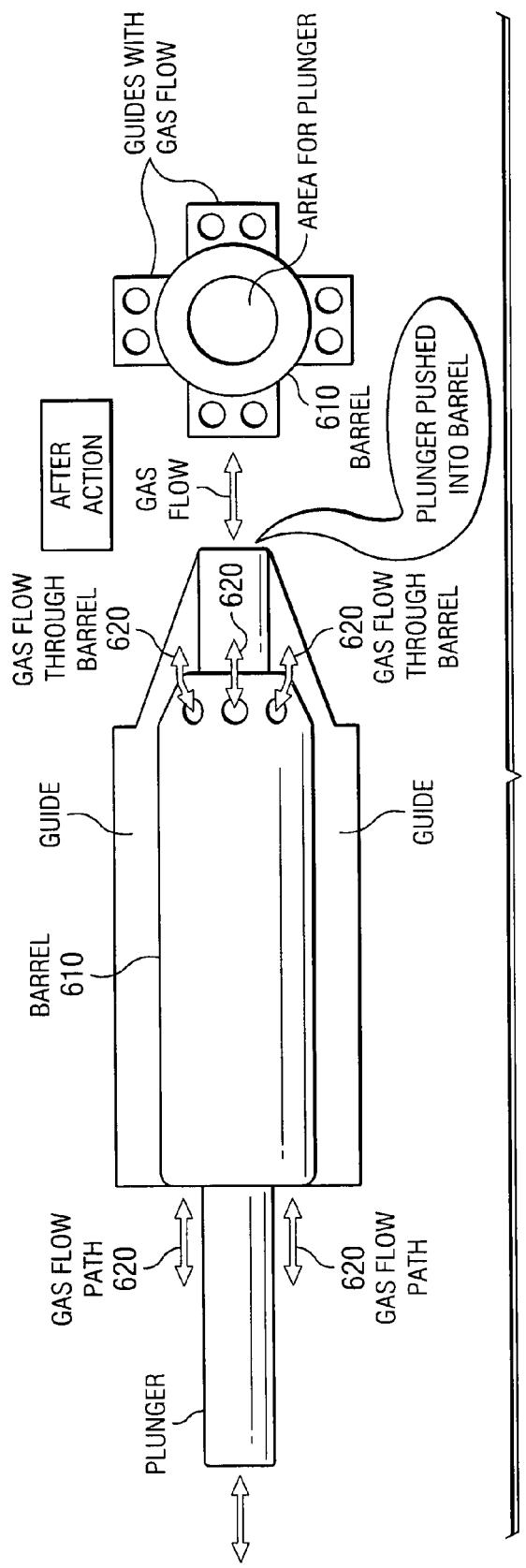

FIGS. 6A and 6B illustrate an example embodiment including a double walled barrel 610 with perforations 615 configured to maintain or augment a first gas flow path 620. The barrel 610 has an inner wall 612 coupled to an outer wall 611 that defines a hollow tube to allow gas to flow through the inner 612 and outer 611 walls of the barrel 610. Thus, in this embodiment, the area between the barrel's inner 612 and outer 611 walls maintain the first gas flow path 620. FIG. 6A illustrates the applicator before a suppository is positioned and FIG. 6B illustrates the applicator after the suppository has been placed in the desired position.

Figure 6C:
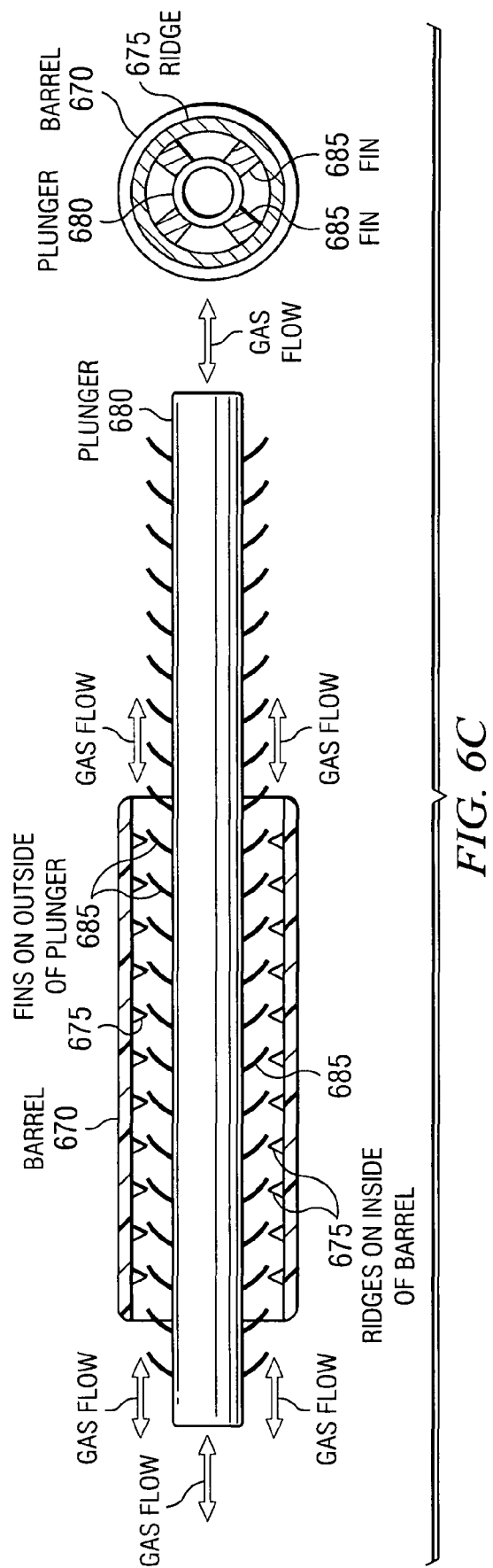

FIG. 6C illustrates yet another alternative example embodiment where the barrel 670 includes ridges 675 along the inner surface of the barrel 670 and the plunger 680 includes fins 685 extending outward from the outer surface of the plunger 680 to the inner surface of the barrel 670. The fins 685 may be configured in a horizontal and/or vertical configuration such that the barrel maintains the first gas flow path. The fins 685 in conjunction with the ridges 675 may increase depth control and placement accuracy.

Figure 7A:
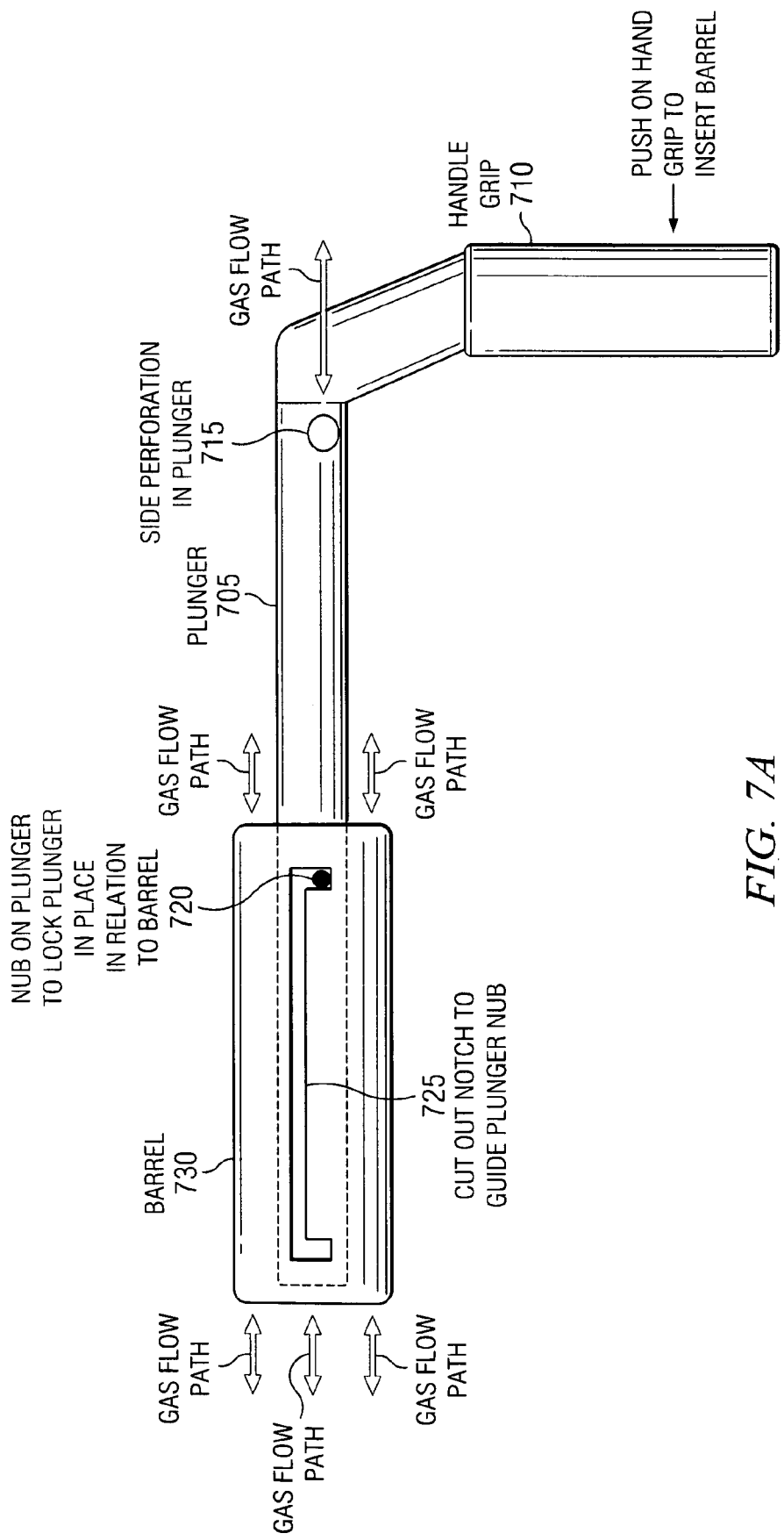
FIGS. 7A-C illustrate alternative example embodiments of the invention configured for use by patients or medical personnel with limited dexterity.
Figure 7B:
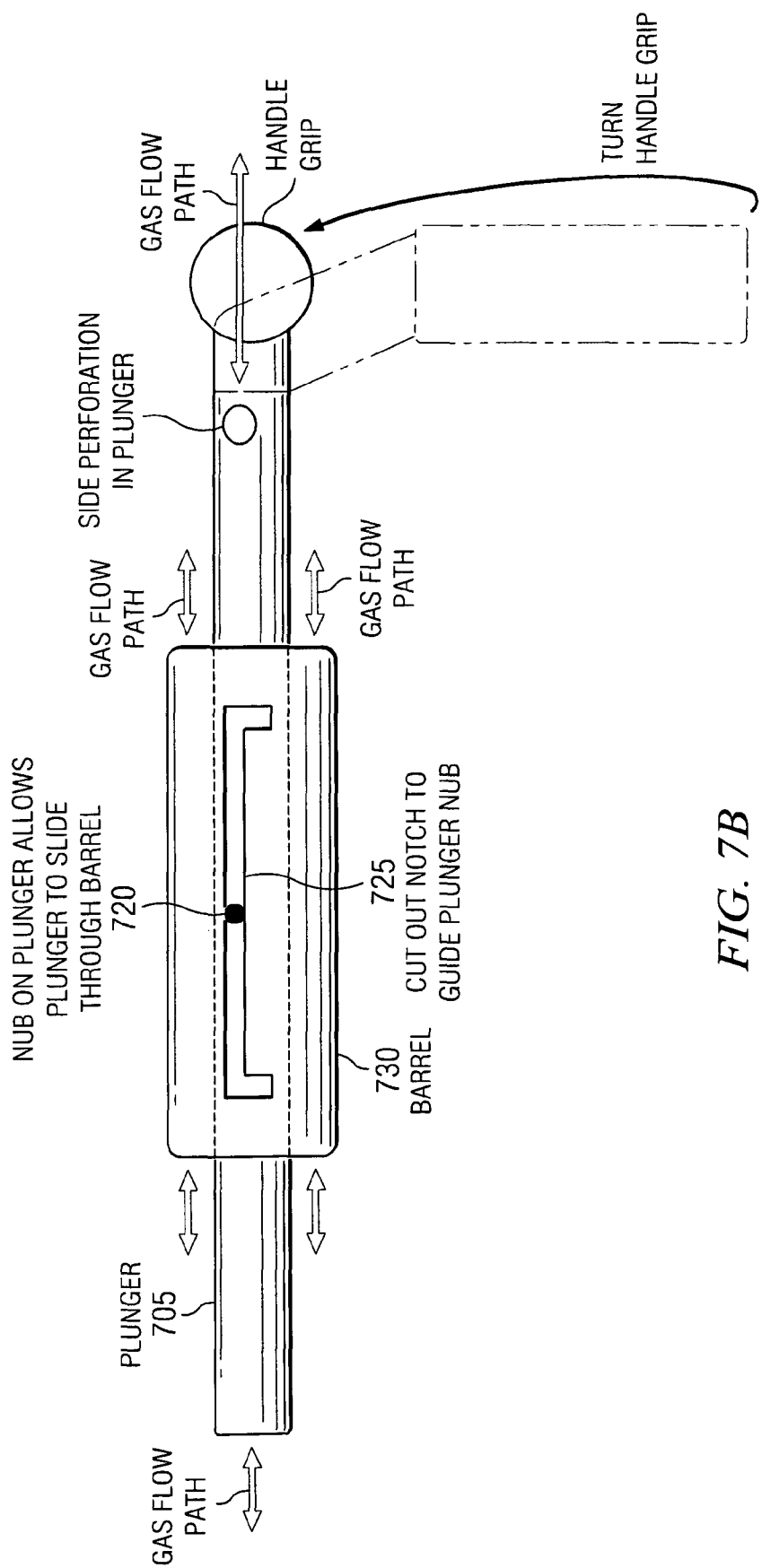
Figure 7C:
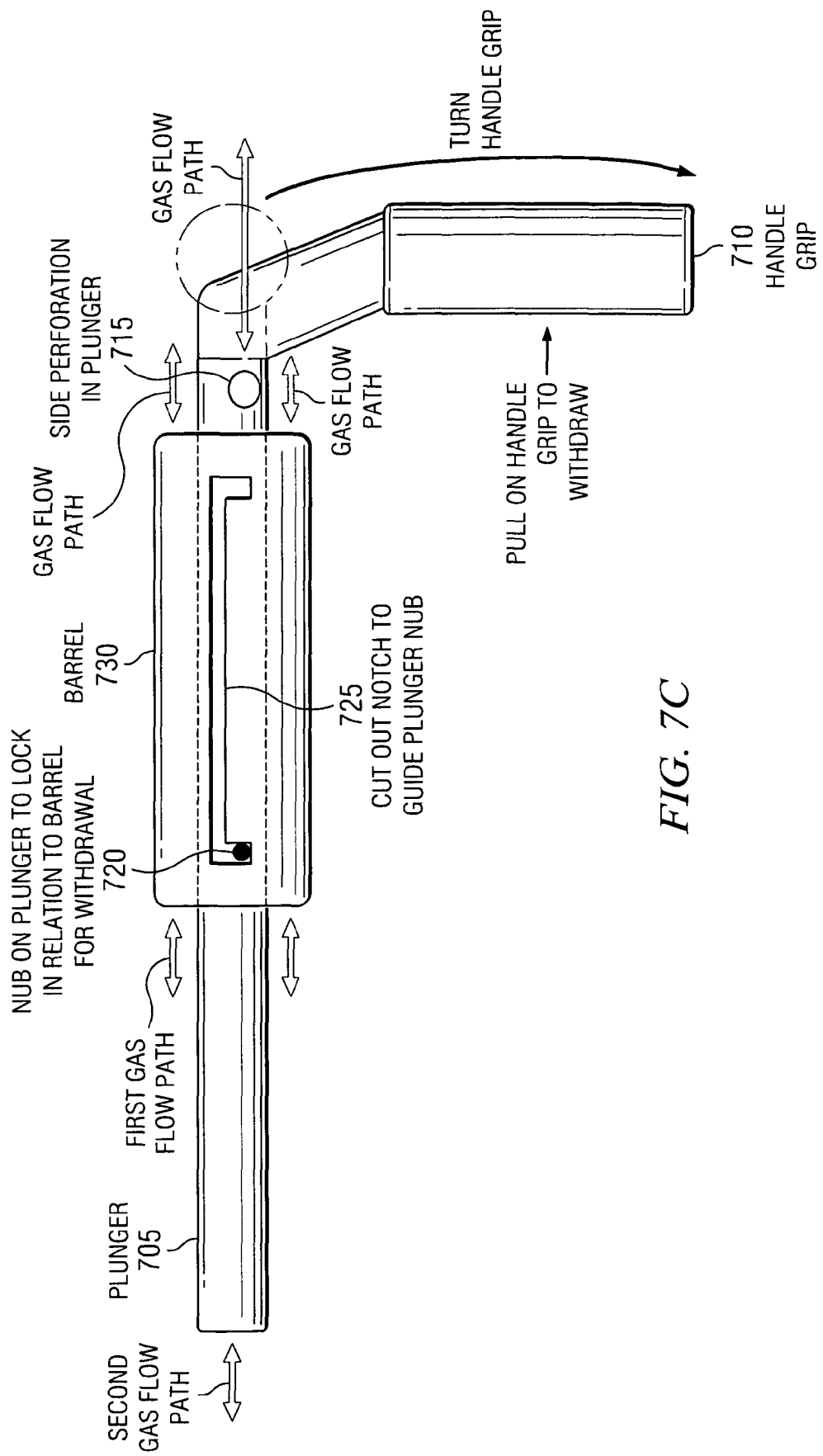

FIG. 7A-C illustrates still another example embodiment of an applicator that provides additional features for use by patients with limited dexterity. In this embodiment, a plunger 705 is movably coupled to a barrel 730 where the plunger 705 includes a handgrip 710 at a hand interface end configured to facilitate manipulation of the plunger 705. The plunger 705 may also include one or more side perforations 715 to maintain or augment a second gas flow path. The plunger 705 may also include a nub 720 that may be configured to slide within a notch 725 formed in the barrel 730. In FIG. 7A, the nub 720 is in a starting position.

FIG. 7B illustrates the nub 720 and notch 725 engagement as the plunger 705 extends through the barrel 730 during insertion of a suppository. To initiate a slidable movement of the plunger 705, the handgrip 710 is rotated to align the nub 720 with the longitudinal section of the notch 725 to release the nub 720 from a starting fixed position to allow the plunger 705 to slide within the barrel 730. The handgrip 710 is depressed until the plunger 705 is fully extended within the barrel 730.

FIG. 7C illustrates the nub 720 locked in a fully extended position after the suppository has been placed into a desired location prior to removal of the applicator. After the hand grip 710 has been fully depressed, it can be locked in a fixed position by rotating the handgrip 710 so that the nub 720 is positioned in the lock position. The applicator may be removed by reversing the procedure.

Figure 8A:
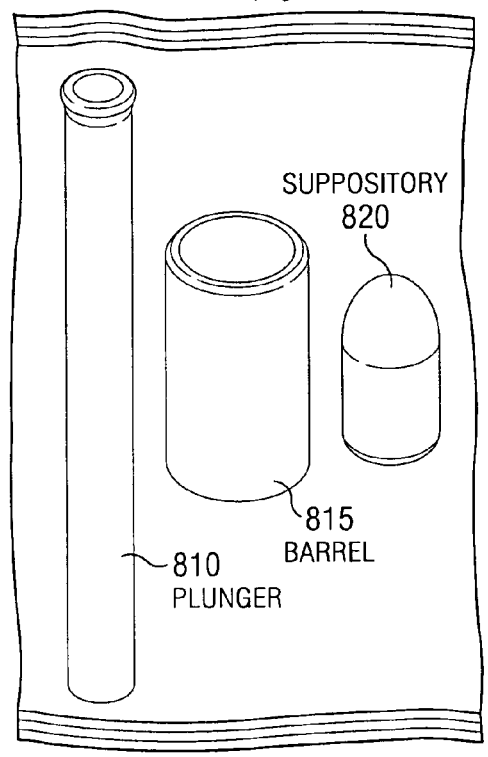
FIGS. 8A-C are perspective views of an apparatus packaged for sanitary use according to example embodiments of the invention.

FIG. 8A illustrates a kit in a packaging container for use in shipping, storing, transporting, and maintaining an applicator configured to insert a rectal suppository in a hygienic and protected state prior to use. The kit may include a plunger 810, barrel 815, and suppository 820. The packaging container may be formed using various materials, such as plastic or foil. For example, the package may include a top and bottom layer of 3-mil plastic sheets heat-sealed at the edges to provide hygienic, airtight package. A notch (not shown) may also be included to allow ease of opening and removal of the applicator. The kit provides a mechanism to conveniently co-locate the items necessary to administer the suppository 820 for home and/or travel use.

Figure 8B:
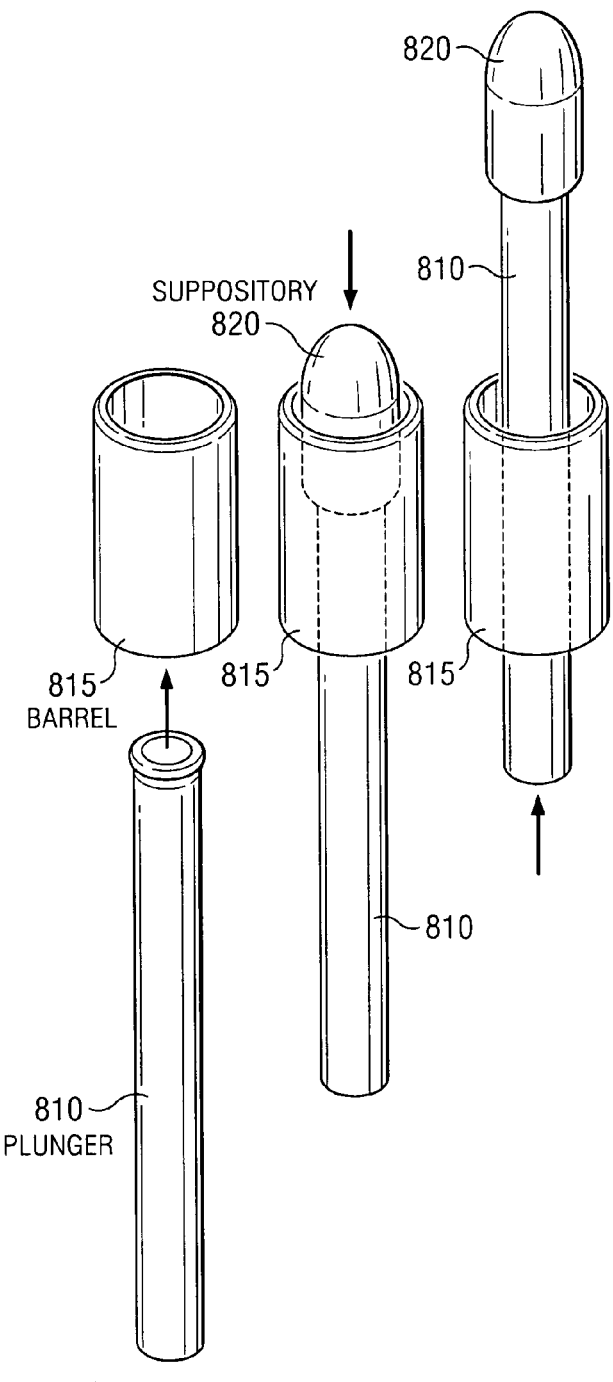

FIG. 8B depicts the applicator in various stages of use. First, the plunger 810 is inserted into the barrel 815. Next, the suppository 820 may be inserted into the barrel 815 in, for example, a suppository holding area (not shown). The barrel 815 is then inserted into the anal canal. The plunger 810 is depressed to position the suppository 820 to the desired location within the anal canal or rectum, for example, above a user's anal trigger zone. Note that during insertion, the barrel 815 maintains a first gas flow path. During withdrawal, the barrel 815 continues to maintain the first gas flow path and the plunger 810 maintains a second gas flow path. Thus, any gas that may have created an air pocket during insertion is allowed to escape and, in addition, any potential suction is similarly alleviated.

It should be noted that although the above sequence describes the plunger 810 being inserted into the barrel 815 as the first step, it may also be possible for the suppository 820 to be inserted into the barrel 810 as a first step. The order in which the components are configured together may be interchangeable and the present invention is not limited by the order thereof.

Figure 8C:
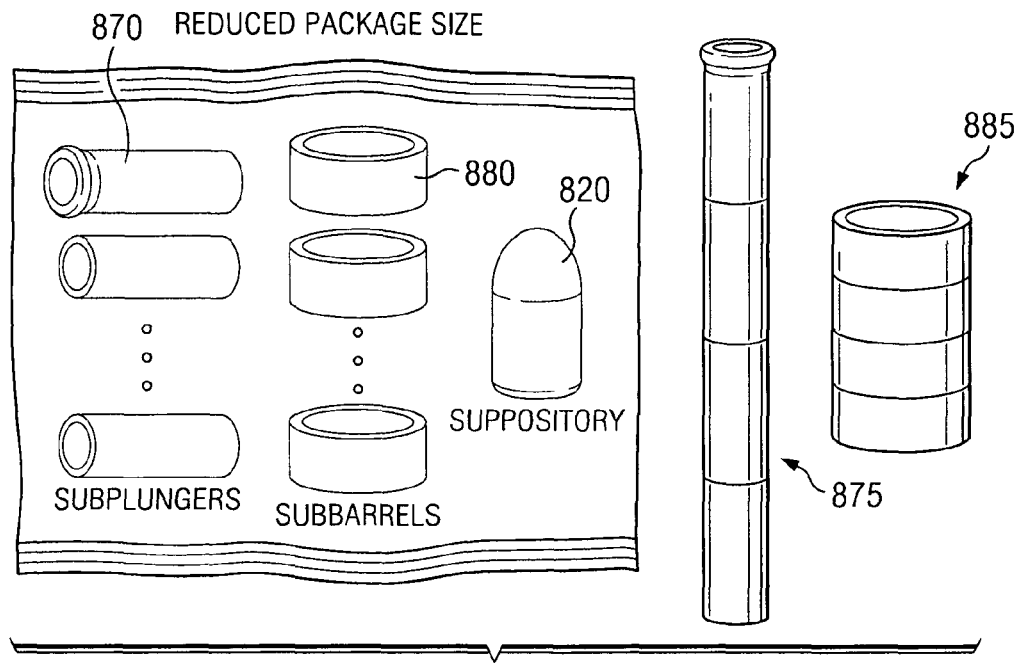

FIG. 8C illustrates an alternative example embodiment of an applicator configured to be packaged in a reduced sized container. Here, the two or more sub-plungers 870 may be assembled to create a single plunger of sufficient length 875. Similarly, two or more sub-barrels 880 may be assembled to create a single barrel 885 of appropriate size where the barrel 885 has a gripper end and an insertion end. Once assembled, the plunger 875 and barrel 885 operate in a similar manner as that described above in various example embodiments. The reduced package size embodiment may be particularly well suited for carrying in, for example, a pocketbook, pocket, or other location on or near a person.

Figure 9:
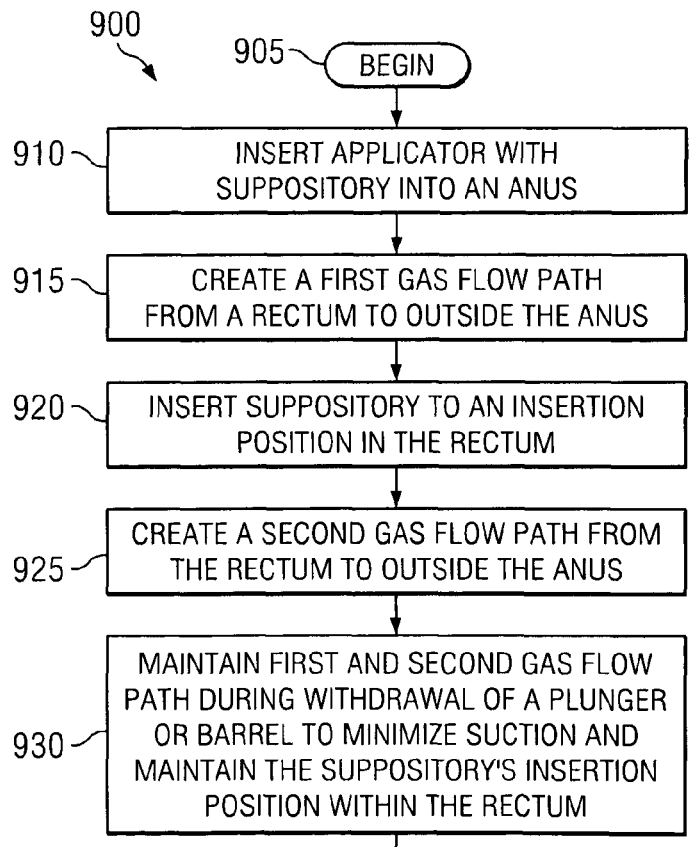
FIG. 9 is a flow diagram illustrating a procedure performed in accordance with an example embodiment of the invention.

FIG. 9 is a flow diagram 900 illustrating an example procedure for inserting a rectal suppository performed in accordance with example embodiments of the present invention. The procedure 900 begins at block 905 and proceeds to block 910 where an application with a suppository are inserted into the anus. At block 915, a first gas flow path extending from a patient's rectum and/or anal canal to outside the patient's anus is created and maintained. At block 920, a suppository is further inserted to a particular insertion position within the patient's rectum while simultaneously maintaining the first gas flow path. At block 925, a second gas flow path extending from the patient's rectum to outside the patient's anus is also created. At block 930, the first and second gas flow paths are maintained as the plunger and/or barrel are withdrawn from the patient so as to minimize suction on the suppository and vent gas, thereby ensuring the suppository maintains the desired insertion position within the rectum and minimizing the gas trapped in the body. It should be noted that the order in which the barrel and plunger are removed can be varied, i.e., the plunger may be removed before, during, or after the barrel is removed. The procedure 900 then ends at block 935.

It should be readily appreciated by those of ordinary skill in the art that the aforementioned blocks are merely examples and that the present invention is in no way limited to the number of blocks or the ordering of blocks described above. For example, some of the illustrated blocks may be performed in an order other than that which is described or include more or fewer blocks. Moreover, it should be understood that various modifications and changes may be made to one or more blocks without departing from the broader scope of the present invention. It should also be appreciated that not all of the illustrated flow diagram is required to be performed, that additional flow diagram(s) may be added or substituted with other flow diagram(s).

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for inserting a rectal suppository into an animal or human, comprising:
   a barrel configured to insert into an anal canal and having ends defining at least one first gas flow path into and out of a body; and
   a plunger defining at least one second gas flow path into and out of the body and configured to be movably coupled to the barrel with the at least one first gas flow path maintained, the plunger movably extendable past an open end of the barrel to insert a suppository into a rectum while maintaining the at least one first gas flow paths during a state of insertion of the suppository into the rectum and maintaining the at least one second gas flow path during withdrawal of the plunger away from the suppository.

2. The apparatus according to claim 1 wherein an insertion end of the plunger is configured to insert the suppository above an anal trigger zone into the rectum to minimize contact of the suppository or its medication with nerves that trigger contraction of anal sphincter muscles to affect the body's ability to retain and absorb the medication.

3. The apparatus according to claim 1 further including at least one gas flow path spacing element configured to maintain the at least one first gas flow path with the plunger movably coupled to the barrel.

4. The apparatus according to claim 3 wherein the barrel includes the at least one gas flow path spacing element, the at least one gas flow path spacing element extending inward from an inner wall of the barrel while maintaining the at least one first gas flow path defined by the barrel to contact an outer wall of the plunger.

5. The apparatus according to claim 3 wherein the plunger includes the at least one gas flow path spacing element, the at least one gas flow path spacing element extending outward from an outer wall of the plunger while maintaining the at least one first gas flow path defined by the barrel to contact an inner wall of the barrel.

6. The apparatus according to claim 3 wherein the barrel includes at least one gas flow path spacing element extending inward while maintaining the at least one first gas flow path defined by the barrel and wherein the plunger includes at least one gas flow path spacing element extending outward while maintaining the at least one first gas flow path.

7. The apparatus according to claim 1 further including at least two flow path spacing elements, defined by at least one gas flow path spacing element extending inward from the barrel and at least one gas flow path spacing element extending outward from the plunger, wherein the at least two flow path spacing elements are configured to interconnect in a movable relationship to each other.

8. The apparatus according to claim 1 wherein the barrel and the plunger are shaped to provide at least one gas flow path between each other with the plunger positioned at least partially within the barrel.

9. The apparatus according to claim 1 wherein the barrel includes at least two sub barrels arrangeable to form the barrel.

10. The apparatus according to claim 1 wherein the plunger includes at least two subplungers arrangeable to form the plunger.

11. The apparatus according to claim 1 wherein the barrel and the plunger each defines a hollow tube.

12. The apparatus according to claim 1 wherein the barrel includes an inner wall that defines a hollow tube and further includes an outer wall coupled to the inner wall by a structure to define the at least one first gas flow path.

13. The apparatus according to claim 1 wherein the plunger defines a non-hollow structure and at least one gas flow path spacing element extending outward from a wall of the structure is configured to press on tissue between the anal canal or rectum and the plunger in a manner defining the at least one second gas flow path.

14. The apparatus according to claim 1 further including a suppository support element configured to support a suppository at least partially inside an open end of the barrel.

15. The apparatus according to claim 1 wherein the plunger includes a suppository interface end and wherein the suppository interface end is as wide or wider than a portion of the suppository with which the interface end is configured to contact.

16. The apparatus according to claim 1 wherein the plunger includes a suppository interface end and wherein the suppository interface end is narrower than a portion of the suppository with which the interface end is configured to contact.

17. The apparatus according to claim 1 wherein the plunger has an insertion end and a hand or finger-interface end and wherein the plunger has a length that enables a user self-administering the suppository to push the plunger with a palm of a hand or finger pad or tip against the hand or finger-interface end.

18. The apparatus according to claim 1 wherein the barrel or plunger is formed from at least one of the following materials: plastic, polycarbonate, epoxy, acrylic, silicon, rubber, polymer, ceramic, metal, cardboard, glass, wood or paper.

19. An apparatus for inserting a suppository into an animal or human, comprising:
   means for creating at least one first gas flow path from an anal canal to outside an anus; and
   means for inserting a suppository to an insertion position into a rectum in a manner maintaining the at least one first gas flow path and creating at least one second gas flow path from the rectum to outside the anus, the at least one first and the at least one second gas flow paths minimizing suction on the suppository during withdrawal of a plunger from a body to enable the suppository to maintain its insertion position within the rectum.

20. A method of enabling controlled manipulation of a rectal suppository, the method comprising:
   encompassing at least a portion of a rectal suppository at an egress end of a first gas flow path having ingress and egress ends;
   enabling displacement of the suppository from the egress end away from the ingress end at least a distance corresponding to a distance between an anus and rectum; and
   maintaining continuity of a first gas flow path during displacement of the suppository and continuity of a second gas flow path following displacement of the suppository to enable controlled manipulation of the suppository.

21. The method as claimed in claim 20 further including maintaining a spacing between the first gas flow path and the second gas flow path.

22. The method as claimed in claim 20 further including maintaining a spacing between a barrel defining the first gas flow path and a plunger defining the second gas flow path.

23. The method as claimed in claim 20 wherein encompassing at least a portion of the suppository includes supporting the suppository at least partially within and below the egress end of the first gas flow path.

24. The method as claimed in claim 20 further including maintaining a cross-sectional shape of the first gas flow path and the second gas flow path as substantially cylindrical pathways.

25. The method as claimed in claim 20 wherein enabling displacement of the suppository further includes enabling a user to push a plunger associated with the second gas flow path with a palm or finger pad or tip.

* * * * *